United States Patent
Schroeder et al.

(10) Patent No.: US 12,157,820 B2
(45) Date of Patent: Dec. 3, 2024

(54) IN-LINE ULTRASONIC CHECK FOR DETECTING THE PARTIAL VULCANIZATION OF A RUBBER MIXTURE IN THE IN SITU SILANIZATION OF BRIGHT FILLERS

(71) Applicant: LANXESS Deutschland Gmbh, Cologne (DE)

(72) Inventors: Andreas Schroeder, Weinheim (DE); Ludwig Graeff, Viernheim (DE); Lars Wawrzinski, Mannheim (DE); Juergen Schilling, Schwetzingen (DE)

(73) Assignee: LANXESS Deutschland GmbH, Cologne (DE)

( * ) Notice: Subject to any disclaimer, the term of this patent is extended or adjusted under 35 U.S.C. 154(b) by 574 days.

(21) Appl. No.: 17/432,399

(22) PCT Filed: Feb. 17, 2020

(86) PCT No.: PCT/EP2020/054006
§ 371 (c)(1),
(2) Date: Aug. 19, 2021

(87) PCT Pub. No.: WO2020/169494
PCT Pub. Date: Aug. 27, 2020

(65) Prior Publication Data
US 2022/0186001 A1  Jun. 16, 2022

(30) Foreign Application Priority Data
Feb. 19, 2019 (EP) .................................... 19157923

(51) Int. Cl.
*B29C 48/03* (2019.01)
*B29C 48/00* (2019.01)
*B29C 48/92* (2019.01)
*C08C 19/25* (2006.01)
*C08L 9/06* (2006.01)
*G01N 29/11* (2006.01)
*G01N 29/34* (2006.01)
*G01N 33/44* (2006.01)

(52) U.S. Cl.
CPC ............... *C08L 9/06* (2013.01); *B29C 48/92* (2019.02); *C08C 19/25* (2013.01); *G01N 29/11* (2013.01); *G01N 29/348* (2013.01); *G01N 33/445* (2013.01); *B29C 48/022* (2019.02); *B29C 2948/92219* (2019.02); *C08L 2205/025* (2013.01); *C08L 2312/08* (2013.01); *G01N 2291/015* (2013.01); *G01N 2291/0235* (2013.01); *G01N 2291/0251* (2013.01)

(58) Field of Classification Search
CPC .. C08L 9/06; C08L 2205/025; C08L 2312/08; B29C 48/92; B29C 48/022; B29C 2948/92219; B29C 48/03; B29C 48/397; B29C 2948/92209; B29C 2948/9238; C08C 19/25; G01N 29/11; G01N 29/348; G01N 33/445; G01N 2291/015; G01N 2291/0235; G01N 2291/0251; G01N 29/032; C08K 3/013; C08K 5/54; C08K 5/5419; C08K 2003/2227; C08K 2003/2241; C08K 2003/2296; C08K 2003/265; C08K 9/06; C08K 5/0025; C08K 3/22; C08K 3/26; C08K 3/34; C08K 3/36; C08K 5/548; C08J 3/248
See application file for complete search history.

(56) References Cited

U.S. PATENT DOCUMENTS

| | | |
|---|---|---|
| 6,313,212 B1 | 11/2001 | Caretta et al. |
| 7,186,768 B2 | 3/2007 | Korth et al. |
| 8,383,155 B2 * | 2/2013 | Bar-Shalom ......... A61K 31/192 |
| | | 426/573 |
| 8,846,816 B2 | 9/2014 | Borkowsky et al. |
| 9,388,290 B2 | 7/2016 | Schroeder et al. |
| 9,546,272 B2 * | 1/2017 | Aepli ....................... C08K 7/14 |
| 2009/0177439 A1 * | 7/2009 | Samples ............. G05B 23/0272 |
| | | 702/182 |
| 2014/0366633 A1 * | 12/2014 | Schroeder ............... G01N 29/11 |
| | | 73/598 |
| 2019/0031866 A1 | 1/2019 | Schroeder et al. |

FOREIGN PATENT DOCUMENTS

WO  WO-2017129471 A1 *  8/2017  ............. C08C 19/25

OTHER PUBLICATIONS

European Search Report from corresponding European Application No. 19157923, dated Aug. 21, 2019, two pages.

* cited by examiner

*Primary Examiner* — Liam J Heincer
*Assistant Examiner* — Zhen Liu
(74) *Attorney, Agent, or Firm* — Nicanor A. Kohncke; Christopher L. McDavid; Ewa M. Wozniak (57) ABSTRACT

The invention relates to a method for checking the silanization of pale-colored fillers, where a mixture comprising at least one silanized pale-colored filler, preferably silanized silica, and comprising at least one rubber is irradiated with ultrasound waves in a frequency range of 4 to 10 MHz, preferably of 5 to 7 MHz, and the signal strength of the ultrasound waves is determined after transmission through the rubber mixture, where the relative attenuation coefficient $\alpha_{rel}$ of the rubber mixture in the frequency range of the ultrasound waves is determined, the standard deviation $\sigma$ of the relative attenuation coefficient $\alpha_{rel}$ is determined, and $\alpha_{rel}$ and $\sigma$ are used for detection of incipient crosslinking of the rubber mixture.

13 Claims, 4 Drawing Sheets

Fig. 4: In-line ultrasound monitoring of the extrudate R1M1; the black line is the relative attenuation coefficient $\alpha_{rel}$(5.8 to 6.2 MHz); the white line is the moving standard deviation $\sigma_g$ of $\alpha_{rel}$ for 8 s.

Fig. 5: In-line ultrasound monitoring of the extrudate R2M1; the black line is the relative attenuation coefficient $\alpha_{rel}$(5.8 to 6.2 MHz); the white line is the moving standard deviation $\sigma_g$ of $\alpha_{rel}$ for 8 s.

Fig. 6: In-line ultrasound monitoring of the extrudate R3M1; the black line is the relative attenuation coefficient $\alpha_{rel}$(5.8 to 6.2 MHz); the white line is the moving standard deviation $\sigma_g$ of $\alpha_{rel}$ for 8 s.

Fig. 7: In-line ultrasound monitoring of the extrudate R4M1; the black line is the relative attenuation coefficient $\alpha_{rel}$(5.8 to 6.2 MHz); the white line is the moving standard deviation $\sigma_g$ of $\alpha_{rel}$ for 8 s.

Fig. 8: In-line ultrasound monitoring of the extrudate R5M1; the black line is the relative attenuation coefficient $\alpha_{rel}$(5.8 to 6.2 MHz); the white line is the moving standard deviation $\sigma_9$ of $\alpha_{rel}$ for 8 s.

IN-LINE ULTRASONIC CHECK FOR DETECTING THE PARTIAL VULCANIZATION OF A RUBBER MIXTURE IN THE IN SITU SILANIZATION OF BRIGHT FILLERS

The invention relates to the technical field of the silanization of pale-colored fillers. The expression pale-colored fillers is understood by the person skilled in the art to mean natural and synthetic mineral fillers which are not based on carbon black, examples being mica, kaolins, chalks, calcium carbonates, talc, zinc oxides, aluminum oxides, titanium dioxides, silica and silicates. In order to improve processability, the pale-colored fillers are hydrophobized by silanization, with a resultant significant improvement in the properties of the elastomeric vulcanizates. In particular in rubber mixtures for tire treads, when the use of silanized fillers is compared with the black filler carbon black the result is improved wet grip and improved rolling resistance, without any increase of tire abrasion.

In the production of, for example, tire tread mixtures, the silica is dispersed batchwise in the rubber in an internal mixer in a first mixing step, with a silanizing agent. By adjustment of the mixing parameters (rotation rate, fill level, temperature control, etc.), the mixing process here is conducted to give a discharge temperature in the range of 140° C. to 160° C. (cf. F. Röthemeyer, F. Sommer; "Kautschuktechnologie Werkstoffe, Verarbeitung Produkte" [Rubber technology: Materials, Processing and Products], Hanser Verlag 2nd revised edition; ISBN 10: 3-446-40480-5; p. 272). In a second mixing step in the internal mixer, the mixture is homogenized in the range of 140° C. to 160° C. Below 140° C., no reaction takes place between the silane and the silica; above 160° C., the silane can undergo incipient crosslinking with the rubber. Mixers used as internal mixers in the rubber industry include internal mixers with a discharge extruder. Methods tested are not only batch production methods but also continuous methods using extruders, as disclosed in DE69728538T2. Silanization in a rubber mixture is termed in-situ silanization. This is described by way of example in EP-A-0911359, and also in EP-A-1 357156.

In-situ silanization requires precise compliance with the temperatures and mixing times (cf. F. Röthemeyer, F. Sommer; "Kautschuktechnologie Werkstoffe, Verarbeitung Produkte" [Rubber technology: Materials, Processing and Products], Hanser Verlag 2nd revised edition; ISBN 10: 3-446-40480-5; p. 272), and these processes are therefore very susceptible to problems. There is therefore a need for very rapid volumetric and representative checks, carried out during the production process (in-line). This is the only way of ensuring that in-situ silanization is reliably controlled, that thermal stressing of the rubber mixture is kept to a low level and that high efficiency of the process is maintained, and that scrap rates are reduced. This is particularly important in the continuous in-situ silanization process which, for reasons including insufficient possibility for in-line testing, has not yet been able to find a secure place in the market.

In contrast to the requirements for the monitoring of in-situ silanization, measurements on uncrosslinked rubber mixtures in the rubber industry can generally only be made several minutes, or even days, after production of the rubber mixture (by what are known as off-line methods), because the measurements are time-consuming and simultaneous measurement of a number of samples requires a large number of expensive measurement apparatuses. The quality of an uncrosslinked rubber mixture has therefore hitherto been merely subjected to spot checks (on <0.1% of the total quantity). The degree of completion of the silanization reaction is typically checked by determining the Mooney viscosity of the spot-check samples of the rubber mixture (cf. F. Röthemeyer, F. Sommer; "Kautschuktechnologie Werkstoffe, Verarbeitung Produkte" [Rubber technology: Materials, Processing and Products], Hanser Verlag 2nd revised edition; ISBN 10: 3-446-40480-5; p. 390). However, the small number of spot-check samples is not representative of the entire rubber mixture.

There are many representative in-line quality-monitoring methods known for the analysis of plastics compounded by extruders, for example NIR, Raman and UV/VIS spectroscopy, where radiation is passed through the samples (cf. Hochrein et al., Plastverarbeiter, September 2009, p. 92). However, when electromagnetic waves are used the carbon black is problematic, because even when the proportions for carbon black are very small the electromagnetic waves are almost completely absorbed. When mechanical pressure waves in the high frequency range >1 MHz (ultrasound waves) are used, in contrast, carbon black causes fewer problems. In this case, however, pale-colored high-density fillers such as silica, kaolin or chalk, are problematic (cf. A. Schröder, L. Gräff, L. Wawrzinski, Rubber World 251 (2015) 28), because these attenuate the ultrasound waves to a greater extent than low-density carbon black. Uncrosslinked rubbers moreover, in contrast to plastics, intrinsically provide relatively high attenuation by virtue of their viscoelastic properties. Because of this high attenuation, when volumetric measurements are made in transmission there is an upper limit for the distance between the transmitting and receiving ultrasound transducer. If this limit is exceeded, no useful measured values are obtained, because the signal/noise ratio is unacceptable.

On the other hand, there is a lower limit for the distance between the ultrasound transducers, because there remains a need for the high-viscosity rubber mixture to flow between the ultrasound transducers. In Rubber World 251 (2015) 28, the use of ultrasound is described as in-line quality-monitoring system for the detection of varying proportions of filler and crosslinker masterbatches with markers, and also the detection of impurities larger than 100 µm and the macrodispersion of fillers, but only up to a proportion of 30 phr of pale-colored fillers. The proportion of pale-colored fillers in rubber mixtures for tire treads is generally at least 50 phr, with a resultant increase of the viscosity of the rubber mixture.

The monitoring of a chemical reaction, namely the crosslinking of an uncrosslinked rubber with sulfur, is described in M. Jaunich, B. Stark, B. Hoster, Polymer Testing 28 (2009) 84. The velocity of sound is used here to monitor the change of crosslinking density. Ultrasound transducers with an average frequency f of 4 MHz are used here. No extrusion of the mixture takes place.

WO2017129471 A1 discloses a method for the checking of silanization which allows in-line monitoring of the in-situ silanization of pale-colored fillers, in particular of precipitated silicas. The method disclosed therein is a method for monitoring the efficacy of silanization reactions. The silanization in that document is carried out at a temperature below 160° C. Higher temperatures, however, permit higher throughputs of the rubber mixtures in the same period of time, and higher throughput permits faster, and therefore less expensive, production of the rubber mixtures. When the silanization is carried out at higher temperatures there is, however, the risk that the rubber mixture undergoes undesirable incipient crosslinking (also termed "scorch") and/or that the silanizing agent decomposes. Under practical conditions, the risk of such incipient crosslinking is substantially greater than an ineffective silanization of a filler surface at lower temperatures. Incipient crosslinking of the rubber mixture is undesirable because it restricts the flowability of the rubber mixture, with resultant problems in the further processing of the rubber mixture.

There was therefore a need for an in-line method for checking of the in-situ silanization of pale-colored fillers, in particular of silicas, where said method permits minimization of cost in the production of rubber mixtures comprising silanized pale-colored fillers.

Inexpensive methods for the production of rubber mixtures with silanized pale-colored fillers are preferably methods with high throughput, preferably characterized by production at a temperature of above 160° C.

The method for checking the in-situ silanization of pale-colored fillers should therefore preferably permit high-throughput production of rubber mixtures comprising silanized pale-colored fillers, particularly preferably at a temperature of above 160° C.

The process for checking the in-situ silanization of pale-colored fillers should more preferably permit detection of the incipient crosslinking of the rubber mixture.

In order to allow extensive feedback to the process-control system, and to permit increased productivity and/or reduced scrap rates in the process, the result of the checking of silanization should preferably be available, at the latest, one minute after discharge from the extruder. The method should preferably also allow representative monitoring, i.e. checking of at least 1% of the rubber mixture comprising at least one silanized pale-colored filler, preferably under production conditions, i.e. at throughputs of ≥5 kg/h. A non-destructive method would be particularly advantageous here. In order to permit use of the method in the production of rubber mixtures for tires, it would be desirable that the presence of carbon black as additional constituent of the rubber mixture has little adverse effect on the quality-monitoring system, preferably no adverse effect.

Method for Checking the Silanization of Pale-Colored Fillers

Surprisingly, the object is achieved via a method for checking the silanization of pale-colored fillers, where a mixture comprising at least one silanized pale-colored filler, preferably silanized silica, and comprising at least one rubber is irradiated with ultrasound waves in a frequency range of 4 to 10 MHz, preferably of 5 to 7 MHz, and the signal strength of the ultrasound waves is determined after transmission through the rubber mixture, where the relative attenuation coefficient $\alpha_{rel}$ of the rubber mixture in the frequency range of the ultrasound waves is determined, the standard deviation $\sigma$ of the relative attenuation coefficient $\alpha_{rel}$ is determined, and $\alpha_{rel}$ and $\sigma$ are used for detection of incipient crosslinking of the rubber mixture.

It is preferable that in the method for checking the silanization of pale-colored fillers the mixture comprising at least one silanized pale-colored filler, preferably silanized silica, and comprising at least one rubber, is extruded and the resultant extrudate is irradiated with sound as described above. The irradiation of the extrudate with sound more preferably takes place in an extruder.

For the purposes of the present invention, the term "extrudate" means either the mixture, during extrusion, comprising at least one silanized pale-colored filler and comprising at least one rubber or the mixture, after extrusion, comprising at least one silanized pale-colored filler and comprising at least one rubber. For the purposes of the present invention, the extrudate is preferably the mixture, during extrusion, comprising at least one silanized pale-colored filler and comprising at least one rubber.

The rubber mixture is produced preferably at a temperature of above 160° C., particularly preferably at a temperature of above 160° C. to 200° C., very particularly preferably at a temperature of above 160° C. to 180° C.

It is preferable that the temperature of the rubber mixture during the irradiation with sound is above the glass transition range of the rubber mixture in the frequency range of the ultrasound waves. The temperature of the rubber mixture during the irradiation with sound is preferably at least 80° C., particularly preferably at least 100° C.

For the purposes of the present invention, the phrase "incipient crosslinking of the rubber mixture" means that covalent bonds, preferably sulfur-containing covalent bonds, have formed between the polymer chains of the at least one rubber and/or between the at least one silanized pale-colored filler and the polymer chains of the at least one rubber. Insofar as the rubber mixture comprises at least one silanizing agent, another meaning of the phrase "incipient crosslinking" for the purposes of the present invention is the formation of covalent bonds, preferably sulfur-containing covalent bonds, between the at least one silanizing agent and the polymer chains of the at least one rubber.

Various parameters can be used to detect incipient crosslinking of the rubber mixture. It is preferable to detect incipient crosslinking of the rubber mixture via the relative attenuation coefficient $\alpha_{rel}$ of the rubber mixture in the frequency range of the ultrasound waves, and the standard deviation $\sigma$ thereof.

It is particularly preferable to detect incipient crosslinking of the rubber mixture via the relative attenuation coefficient $\alpha_{rel}$ of the rubber mixture in the frequency range of the ultrasound waves and the moving standard deviation $\sigma_g$ thereof.

It is preferable to detect incipient crosslinking of a rubber mixture which is produced at a temperature of above 160° C.

It is preferable that the standard deviation $\sigma$ of the relative attenuation coefficient $\alpha_{rel}$ of the incipiently crosslinked rubber mixture is based on a measurement time of 1 to 500 s, particularly preferably of 1 to 100 s, very particularly preferably 1 to 50 s, most preferably of 1 to 15 s.

It is particularly preferable that the moving standard deviation $\sigma_g$ of the relative attenuation coefficient $\alpha_{rel}$ of the incipiently crosslinked rubber mixture is based on a measurement time of 1 to 100 s, particularly preferably of 1 to 50 s, very particularly preferably of 1 to 15 s.

It is preferable that incipient crosslinking of the rubber mixture is detected in that the standard deviation $\sigma$ of the relative attenuation coefficient $\alpha_{rel}$ of the incipiently crosslinked rubber mixture, preferably produced at a temperature of above 160° C., is above 0.5 [1/m], preferably above 1 [1/m], preferably based on a measurement time of 1 to 500 s, particularly preferably 1 to 100 s, very particularly preferably 1 to 50 s, most preferably 1 to 15 s, and the relative attenuation coefficient $\alpha_{rel}$ of the incipiently crosslinked rubber mixture, preferably produced at a temperature of above 160° C., is below 0 [1/m], particularly preferably below −15 [1/m].

It is particularly preferable that the incipient crosslinking of the rubber mixture is detected in that the moving standard deviation $\sigma_g$ of the relative attenuation coefficient $\alpha_{rel}$ of the incipiently crosslinked rubber mixture, produced at a temperature of above 160° C., is above 1 [1/m], based on a measurement time of 1 to 50 s, preferably of 1 to 15 s, and the relative attenuation coefficient $\alpha_{rel}$ of the incipiently crosslinked rubber mixture, produced at a temperature of above 160° C., is below 0 [1/m], preferably below −15 [1/m].

For the purposes of the present invention, it is preferable that the incipient crosslinking of the rubber mixture is characterized in that the viscosity of the rubber mixture increases as incipient crosslinking proceeds.

It is preferable that the Mooney ML 1+4 (100° C.) viscosity of an incipiently crosslinked rubber mixture is greater by at least 5 MU (Mooney units) than that of a reference rubber mixture that has not yet been incipiently crosslinked, with identical composition.

For the purposes of the present invention, the phrase "a reference rubber mixture that is not yet incipiently crosslinked" means a rubber mixture which has not been incipiently crosslinked and has the same composition and was produced at a temperature of at least 140° C. to 160° C., preferably in the same mixing assembly, particularly preferably with the same number of mixing stages, when compared with an incipiently crosslinked rubber mixture for which it serves as reference. It is particularly preferable that in the reference rubber mixture that is not yet incipiently crosslinked more than 90% by weight of the at least one pale-colored filler, preferably more than 95% by weight, particularly preferably more than 99% by weight, has been silanized.

More preferably, the ultrasound amplitude of the reference rubber mixture that is not yet incipiently crosslinked is determined at a temperature, pressure and shear rate that are the same as those used for the incipiently crosslinked rubber mixture.

For the purposes of this invention it is preferable that the storage modulus G' of the incipiently crosslinked rubber mixture, measured by the RPA 2000 from Alpha Technologies at 1% tensile strain amplitude at a frequency of 1 Hz and a temperature of 60° C., is the same as or less than, particularly preferably less than, the modulus G' of the reference rubber mixture that is not yet incipiently crosslinked.

It is preferable that the method of the invention is a method for detecting incipient crosslinking of the rubber mixture.

It is preferable that the process of the invention is an in-line process, because the checking of the silanization takes place during the process of production of the rubber mixture.

It is preferable that the process of production of the rubber mixture ends after discharge of the extrudate from the extruder.

The following are in particular suitable as rubbers: natural rubber (NR), isoprene rubber (IR), styrene-butadiene rubber (SBR), butadiene rubber (BR), isoprene-isobutylene rubber (IIR), polychloroprene rubber (CR), acrylonitrile-butadiene rubber (NBR), hydrogenated acrylonitrile-butadiene rubber (HNBR), carboxylated acrylonitrile-butadiene rubber (XNBR), hydrogenated carboxylated acrylonitrile-butadiene rubber (HXNBR), ethylene-propylene-diene rubber (EPDM), ethylene-propylene rubber (EPM), fluoro rubber (FKM), perfluorinated fluoro rubber (FFKM), acrylate-ethylene rubber (AEM), acrylate rubber (ACM), ethylene-methylene-acrylate rubber (EMA), chlorinated polyethylene, chlorosulfonated polyethylene, ethylene-vinyl acetate rubber (EVA), silicone rubber, fluorosilicone rubber, ethylene-epichlorohydrin rubber (ECO), epichlorohydrin rubber (CO) and/or polyurethane rubber (PU).

It is particularly preferable that the at least one rubber is selected from the group consisting of natural rubber (NR), isoprene rubber (IR), styrene-butadiene rubber (SBR) and butadiene rubber (BR), very particularly preferably styrene-butadiene rubber (SBR) and butadiene rubber (BR).

Preferred pale-colored fillers for the purposes of the invention are mica, kaolin, siliceous earth, calcium carbonates, zinc oxides, aluminum oxides, titanium dioxides, silicas, chalk and talc, particularly preferably silicas and most preferably precipitated silicas.

In a specific embodiment of the present invention it is possible to use what are known as dual phase fillers as pale-colored filler. These are carbon black particles with a proportion of >5% of silicas; these are known to the person skilled in the art.

Silanization is chemical linkage of a silane to the surface of the pale-colored filler. The linkage is achieved via condensation reactions between hydrolysable groups of the silanes used and chemical groups on the surface of the pale-colored filler.

It is preferable that the at least one silanized pale-colored filler is produced from at least one pale-colored filler and at least one silanizing agent.

In a preferred embodiment, the production of the at least one silanized pale-colored filler from at least one pale-colored filler and at least one silanizing agent takes place in an extruder.

It is preferable that a silane is used as the at least one silanizing agent. Preference as silane is given to bifunctional silanes where a functional group can react with the surface of a pale-colored filler, examples being trialkoxysilyl groups, and where the other functional group can participate in the crosslinking reaction of the rubber, an example being thiol or polysulfane groups.

Particular preference is given to the following silanes:

Bis(3-triethoxysilylpropyl) tetrasulfide (available commercially by way of example as Si69® from Evonik Industries AG), bis(triethoxysilylpropyl) disulfide (available commercially by way of example as Si75® from Evonik Industries AG), bis(triethoxysilylpropyl) disulfide (available commercially by way of example as Si266® from Evonik Industries AG), 3-thiocyanatopropyltriethoxysilane (available commercially by way of example as Si264™ from Evonik Industries AG), 3-mercaptopropyldi(tridecan-1-oxy-13-penta(ethylene oxide))ethoxysilane (available commercially by way of example as VP Si 363® from Evonik Industries AG) and gamma-mercaptopropyltrimethoxysilane.

Very particular preference is given to the silane bis(3-triethoxysilylpropyl) tetrasulfide.

The rubber mixture can comprise not only the at least one silanized pale-colored filler and the at least one rubber but also at least one pale-colored filler and/or at least one silanizing agent.

As the silanization of the at least one pale-colored filler proceeds, the proportion of at least one pale-colored filler and of at least one silanizing agent in the rubber mixture decreases, and the proportion of at least one silanized pale-colored filler increases.

Because the at least one silanized pale-colored filler and the at least one silanizing agent are capable of incipient crosslinking of the rubber, they can be regarded as crosslinking agents.

The rubber mixture preferably comprises less than 10 phr of crosslinking agent other than the at least one silanizing agent and the at least one silanized pale-colored filler, particularly preferably less than 5 phr, very particularly preferably less than 2 phr. The rubber mixture most preferably comprises no crosslinking agents other than the at least one silanizing agent and the at least one silanized pale-colored filler.

The proportion of pale-colored fillers in the rubber mixture is typically 20 to 250 phr, preferably 30 to 150 phr and particularly preferably 40 to 100 phr.

In an embodiment of the method of the invention, the rubber mixtures are analyzed by at least one pair, preferably by at least one detection band of at least two pairs, of ultrasound transducers. The respective transducers of a pair are opposite to one another, and the pairs are arranged alongside one another in series.

One ultrasound transducer of a pair functions here as transmitter, and the other transducer functions as receiver of the ultrasound signal. In the transmitter, voltage pulses generated in the electronic check system are converted into ultrasound waves with the aid of the piezoelectric effect. The shape of a voltage pulse during excitation of the transmitter is typically that of a rectangular pulse or of a needle pulse. It is preferable to use at least two voltage pulses in succession (a burst signal) with a time interval of $\geq 0.1$ µs and $\leq 1$ µs, and it is particularly preferable to use at least three voltage pulses, very particularly preferably at least seven voltage pulses. It is particularly preferable that the reciprocal of the time interval between the voltage pulses of a burst signal corresponds to the intrinsic frequency of the ultrasound transducers used. It is preferable that emission of an ultrasound signal consisting of a single voltage pulse or of burst signals is repeated with a frequency of at least one 1 Hz, particularly preferably at least 10 Hz. In the receiver, the ultrasound waves are converted back to voltage signals during extrusion, after transmission through the rubber mixture, and can be quickly evaluated, preferably in less than 1 min.

The rubber mixture is present in the gap between the ultrasound transducers. There is preferably direct contact here between the ultrasound transducers and the rubber mixture. The gap is preferably delimited at the sides, thus producing a flow channel with a height of $\geq 5$ mm, particularly preferably with a height of $\geq 10$ mm. The width of the flow channel is preferably $\geq 15$ mm, particularly preferably $\geq 20$ mm. The rubber mixture flows through the detection band with a velocity of preferably 0.1 m/min or above, particularly preferably 1 m/min or above, very particularly preferably 10 m/min or above. In a preferred embodiment, an extruder is used for this purpose. It is preferable that the flow channel is a constituent of the extruder. A portion of the rubber mixture here, preferably more than 1% by volume, with preference more than 10% by volume, with particular preference more than 25% by volume of the rubber mixture, is analyzed by the ultrasound. It is thus possible to obtain representative checking, rather than merely spot-checking, of the silanization of rubber mixtures.

It is preferable that the distance between a transmitter emitting the ultrasound waves and a receiver receiving the ultrasound waves is at least 5 mm, particularly preferably 5 mm to 15 mm.

The pressure in the rubber mixture between the acoustic transducers during the irradiation with sound is preferably at least 10 bar, particularly preferably at least 30 bar, very particularly preferably between 50 and 100 bar.

It is preferable to use ultrasound waves in the frequency range of 5 to 7 MHz. Ultrasound waves of one or more frequencies f can be used for the measurement. If a frequency spectrum is applied to the material, the use of ultrasound waves in the range of, for example, 5 to 7 MHz typically means that for the emitted ultrasound frequency f the arithmetic average of the boundary frequencies, i.e. of the lower and the upper frequency at which the ultrasound wave amplitude or the ultrasound wave intensity is 50% of the maximal value, is from 5 to 7 MHz.

In a preferred embodiment of the invention, the amplitude of the soundwaves converted to voltage signals is measured as a function of the time elapsed since emission of the acoustic signal in the transmitter. These "A scans" are recorded as a function of time.

In an embodiment of the invention, for quantification of the signal strength of the ultrasound waves, the value of an ultrasound wave amplitude, preferably the maximal ultrasound wave amplitude, is determined from the ultrasound signal of an A scan, and the logarithm of the ultrasound wave amplitude a is plotted against the time t.

It is preferable that the ultrasound signal of an A scan is evaluated, rather than the echo of the ultrasound signal.

In another embodiment of the invention, the ultrasound wave intensity i is determined by calculating the square of the ultrasound wave amplitude a, and the logarithm of the ultrasound wave intensity i is plotted against the time t.

The relative attenuation coefficient $\alpha_{rel}$ is preferably determined in accordance with the formula (1a)

$$\alpha_{rel}=(\ln a_{ref}-\ln a)/x=(\ln i_{ref}-\ln i)/2x \tag{1a}$$

from the ultrasound wave amplitude a and the ultrasound wave amplitude $a_{ref}$ of a reference and the distance x between the ultrasound transducers. Alternatively, it is possible to determine the relative attenuation coefficient $\alpha_{rel}$ from the ultrasound wave intensity i, ultrasound wave intensity $i_{ref}$ of a reference and the distance x between the ultrasound transducers.

It is preferable to use as reference a rubber mixture with the same composition as the rubber mixture that is to be checked.

It is very particularly preferable to use as reference the reference rubber mixture that is not yet incipiently crosslinked.

In another preferred embodiment, the signal strength of the ultrasound wave signal of the reference is determined during extrusion by extruding at least 1 kg of a rubber mixture under comparable processing conditions and measurement conditions. Comparable processing conditions and measurement conditions are present during extrusion and measurement if the changes of throughput are less than 10%, the changes of the temperature of the extrudate between the ultrasound transducers are less than ±5 K, and changes of the pressure p in the extrudate between the ultrasound transducers are less than ±5 bar. Preference is given to processing conditions and measurement conditions when the changes of throughput are less than 5%, the changes of the temperature of the extrudate between the ultrasound transducers are less than ±2 K, and changes of the pressure in the extrudate between the ultrasound transducers are less than ±2 bar. Particular preference is given to processing conditions and measurement conditions when the changes of throughput are less than 2%, the changes of the temperature of the extrudate between the ultrasound transducers are less than ±1 K, and changes of the pressure in the extrudate between the ultrasound transducers are less than ±1 bar.

In another embodiment of the invention, the values of the ultrasound signal are squared and then integrated, and the integral of the ultrasound wave intensity I is thus determined.

Alternatively, the integrated ultrasound wave amplitude A can be determined from the square root of the ultrasound wave intensity I.

The relative attenuation coefficient $\alpha_{rel}$ is particularly preferably determined in accordance with the formula (1b) with the aid of the integrated ultrasound wave intensity I and, respectively, the integrated ultrasound wave amplitude A.

$$\alpha_{rel} = (\ln A_{ref.} - \ln A)/x = (\ln I_{ref.} - \ln I)/2x \qquad (1b)$$

In a preferred embodiment of the invention, Fast Fourier Transformation (FFT) is used to determine the frequency spectrum a(f) of the ultrasound wave amplitude and, respectively, of the ultrasound wave intensity i(f).

The relative attenuation coefficient $\alpha_{rel}$ is preferably determined as a function of the frequency f in accordance with the formula (1c)

$$\alpha_{rel}(f) = (\ln a_{ref.}(f) - \ln a(f))/x = (\ln i_{ref.}(f) - \ln i(f))/2x \qquad (1c)$$

from the ultrasound wave amplitude a(f), the ultrasound wave amplitude $a_{ref.}(f)$ of a reference and, respectively, from the ultrasound wave intensity i(f), the ultrasound wave intensity $i_{ref.}(f)$ of a reference, and the distance x between the ultrasound transducers.

In a particularly preferred embodiment of the invention, the frequency spectrum is subdivided into frequency ranges with a minimal frequency of $f_{min.}$ and a maximal frequency $f_{max.}$, and integrated. It is preferable that these frequency ranges comprise a maximum of the ultrasound wave amplitude and, respectively, the ultrasound wave intensity.

The relative attenuation coefficient $\alpha_{rel}$ is preferably determined as a function of the frequency range from, and including, $f_{min.}$ to, and including, $f_{max.}$ in accordance with the formula (1d)

$$a_{rel}(f_{min.}, f_{max.}) = (\ln A_{ref.}(f_{min.}, f_{max.}) - \ln A(f_{min.}, f_{max.}))/x = (\ln I_{ref.}(f_{min.}, f_{max.}) - \ln I(f_{min.}, f_{max.}))/2x \qquad (1d)$$

from the ultrasound wave amplitude $A(f_{min.}, f_{max.})$, the ultrasound wave amplitude $A_{ref.}(f_{min.}, f_{max.})$ of a reference and the distance x between the ultrasound transducers. Alternatively, the relative attenuation coefficient $\alpha_{rel}$ can be determined from the ultrasound wave intensity $I(f_{min.}, f_{max.})$, ultrasound wave intensity $I_{ref.}(f_{min.}, f_{max.})$ of a reference and the distance x in accordance with the formula (1d).

The standard deviation a of the relative attenuation coefficient $\alpha_{rel}$ is determined by the methods known to the person skilled in the art from the measured values, preferably during extrusion, for a particular number n of measured values in chronological succession. The measurement time for the standard deviation is obtained from the number of measured values n and the constant time interval between the measurements. The average value $\overline{\alpha_{rel}}$ of the relative attenuation coefficient in the measurement time is first determined in accordance with formula (1e). The sum of the square of the difference between the individual measured values in the measurement time and the average value, divided by the total number n of measured values, is the variance $\sigma^2$ of the relative attenuation coefficient in the measurement time. The root of the variance is the standard deviation a of the relative attenuation coefficient $\alpha_{rel}$ (formula (1f)).

$$\overline{\alpha_{rel}} = \sum_0^n \alpha_{rel}(n) \qquad (1e)$$

$$\sigma = \sqrt{\frac{\sum_0^n (\alpha_{rel}(n) - \overline{\alpha_{rel}})^2}{n}} \qquad (1f)$$

The relative attenuation coefficient $\alpha_{rel}$ is preferably determined at the intrinsic frequency of the ultrasound transducers.

In a preferred embodiment, the distance x between the ultrasound transducers is determined with a tolerance below or equal to 0.1 mm with the aid of inside calipers.

The number of measured values used for determination of the standard deviation $\sigma$ of the relative attenuation coefficient $\alpha_{rel}$ is preferably below 1000, particularly preferably below 100, very particularly preferably below 20.

It is preferable to determine the moving standard deviation $\sigma_g$ of the relative attenuation coefficient $\alpha_{rel}$. The moving standard deviation $\sigma_g$ is calculated in accordance with formula (1h) from the moving average of $\alpha_{rel}$, calculated in accordance with formula (1g). The variables x and y in the formulae (1g) and (1h) are the upper and, respectively, the lower boundary of the time interval for determination of the moving standard deviation $\sigma_g$.

$$\overline{\alpha_g} = \sum_{n-y}^{n+x} \alpha_{rel}(n) \qquad (1g)$$

$$\sigma_g = \sqrt{\frac{\sum_{n-y}^{n+x} (\alpha_{rel}(n) - \overline{\alpha_g})^2}{n}} \qquad (1h)$$

In another embodiment, the velocity $V_S$ of sound in the rubber mixture is determined in accordance with formula (2), alongside determination of the relative attenuation coefficient.

$$V_S = x/(t_{oF} - t_{US}) \qquad (2)$$

The time required by the ultrasound signal between the juncture of emission in the transmitter and reception in the receiver is $t_{oF}$. The time required by the ultrasound signal in the ultrasound transducers is $t_{US}$. The time $t_{US}$ is determined at ultrasound-transducer temperatures that are preferably comparable to those during extrusion. The time $t_{US}$ is determined by determining $t_{oF}$ at varying distance x between the ultrasound transducers. It is preferable here to use the reference between the ultrasound transducers. It is preferable to set at least four distances in the range of 5 mm to 30 mm. The time $t_{US}$ is obtained from the axis intercept of a linear regression of the plot of $t_{oF}$ against the distance x between the ultrasound transducers.

Insufficiently silanized pale-colored fillers lead to a decrease of the ultrasound wave amplitude a and, respectively, of the ultrasound intensity i at the receiver and to an increase of the relative attenuation coefficient $\alpha_{rel}$. The velocity $V_S$ of sound remains unchanged. The standard deviation a of the relative acoustic attenuation coefficient $\alpha_{rel}$ indicates the homogeneity of the rubber mixture.

In a preferred embodiment, the rubber mixture passes through a detection band of one or more ultrasound sensor pairs arranged across the full width of the flow channel.

In a particularly preferred embodiment, the rubber mixture passes through two detection bands arranged with slight offset. The advantage of this is that a major portion of the rubber mixture is analyzed, preferably the entire rubber mixture.

Device

The invention also further comprises a device comprising an arrangement of an extruder, at least one detection band of at least two ultrasound sensor pairs arranged adjacent to one another, and at least one evaluation unit for the conduct of the method of the invention for checking the silanization of pale-colored fillers. The detection band is preferably a constituent of the extruder.

Preferred embodiments of the device of the invention are depicted in FIG. 1 to FIG. 3.

METHOD FOR THE PRODUCTION OF A RUBBER MIXTURE COMPRISING AT LEAST ONE SILANIZED PALE-COLORED FILLER

The invention further provides a method for the production of a rubber mixture comprising at least one silanized pale-colored filler where, at a temperature of above 160° C., at least one pale-colored filler is mixed with at least one rubber and with at least one silanizing agent, and where at least a portion of the resultant rubber mixture is checked by the method of the invention for checking the silanization.

It is preferable that more than 1% by volume, particularly preferably more than 10% by volume, very particularly preferably more than 25% by volume, very very particularly preferably more than 50% by volume, most preferably more than 80% by volume, of the resultant rubber mixture is checked by the method of the invention for checking the silanization.

The production method is preferably implemented at a temperature of above 160° C. to 200° C., particularly preferably of above 160° C. to 180° C.

The above method is preferably a method for the production of a rubber mixture comprising at least one silanized pale-colored filler, where at least one pale-colored filler is mixed with at least one rubber and at least one silanizing agent at a temperature of above 160° C., and where at least a portion of the resultant rubber mixture is checked by the method of the invention for checking the silanization, and where the moving standard deviation $\sigma_g$ of the relative attenuation coefficient $\alpha_{rel}$ of the rubber mixture is below 0.5 [1/m], preferably below 0.3 [1/m], based on a measurement time of 1 to 100 s, preferably of 1 to 50 s, particularly preferably 1 to 15 s, and the relative attenuation coefficient $\alpha_{rel}$ of the rubber mixture is below 0 [1/m], preferably below −5 [1/m], particularly preferably below −5 [1/m] and equal to or above −15 [1/m].

It is preferable that the rubber mixture obtained by the abovementioned preferred method has not yet been incipiently crosslinked.

The method of the invention can be operated here continuously or as batch method.

In a preferred embodiment, the method for the production of a rubber mixture comprising at least one silanized pale-colored filler is implemented before the extrusion of the resultant rubber mixture, and the method for checking the silanization is implemented by irradiation with sound, in an extruder, of the extrudate obtained by the extrusion.

In another preferred embodiment, the method for the production of a rubber mixture comprising at least one silanized pale-colored filler and the method of the invention for checking the silanization are implemented in the same extruder. In this case, at least one pale-colored filler, at least one silanizing agent and at least one rubber are introduced into the extruder and the silanized pale-colored filler is formed therein from the silanizing agent and the pale-colored filler.

In the last-mentioned embodiment it is optionally possible that at least one pale-colored filler, at least one rubber and at least one silanizing agent are premixed at a temperature of below or equal to 160° C. within or outside of the extruder, and that this mixture is then irradiated with sound in the extruder.

The descriptions and preferred ranges mentioned at an earlier stage above in relation to the method of the invention for checking the silanization apply analogously to the components used in the method for the production of a rubber mixture comprising at least one silanized pale-colored filler, where said components include, but are not restricted to, the at least one pale-colored filler, the at least one rubber and the at least one silanizing agent.

In the process for the production of a rubber mixture comprising at least one silanized pale-colored filler it is preferable to use 5 to 15% by weight of at least one silanizing agent, based on the total content of pale-colored fillers in the rubber mixture.

Other Additional Substances

The rubber mixtures comprising at least one silanized pale-colored filler can comprise other additional substances, for example other fillers, other additives such as aging inhibitors, plasticizers, other crosslinking agents, vulcanization accelerators and/or vulcanization retarders and/or other auxiliaries.

For the purposes of the present invention, the phrase "other fillers" means fillers other than the at least one pale-colored filler described in more detail at an earlier stage above and the at least one silanized pale-colored filler.

Examples of other fillers are carbon-based fillers, e.g. carbon black, graphite, carbon nanotubes, and also magnetizable fillers such as carbonyl iron powder, iron oxides, ferrites and/or fibers, e.g. aramid fiber pulp and carbon fibers.

The following are suitable as aging retarders: coloring and noncoloring aging retarders, e.g. paraphenylenediamines, isopropylphenylparaphenylenediamine (IPPD), para-phenylenediamine (6PPD), N,N-ditolyl-p-phenylenediamine (DTPD), amines, e.g. trimethyl-1,2-dihydroquinoline (TMQ), [(phenyl)amine]-1,4-naphthalenedione (PAN), bis (4-octylphenyl)amine (ODPA), styrenated diphenylamine (SDPA), mono- and bisphenols, e.g. 2,2'-methylenebis(4-methyl-6-tert-butylphenol (BPH), 2,2'-isobutylidenebis(4,6-dimethylphenol) (NKF), 2,2'-dicyclopentadienylbis(4-methyl-6-tert-butylphenol) (SKF), 2,2'-methylenebis(4-methyl-6-cyclohexylphenol (ZKF), 2,6-di-tert-butyl-p-cresol (BHT), substituted phenol (DS), styrenated phenols (SPH), mercaptobenzimidazoles, e.g. 2-mercaptobenzimidazole (MBI), 2-mercaptomethylbenzimidazoles (MMBI), zinc 4- and 5-methyl-2-mercaptobenzimidazoles (ZMMBI).

Examples of plasticizers are long-chain esters and/or ethers, for example thioesters, phthalic esters, alkylsulfonic esters, adipic esters, sebacic esters, dibenzyl ethers, and/or mineral oils (paraffinic, aromatic naphthenic or synthetic oils).

For the purposes of the present invention, the phrase "other crosslinking agents" means crosslinking agents other than the at least one silanized pale-colored filler described in more detail at an earlier stage above and the at least one silanizing agent.

Other crosslinking agents can be:
network node-formers: network node-formers are molecules which are capable of bonding two individual polymer chains to one another, e.g.
  sulfur (soluble or insoluble) and/or sulfur donors, e.g. dithiodimorpholines (DTDM), tetramethylthiu ram disulfides (TMTD), tetraethylthiuram disulfide (TETD), dipentamethylenethiuram tetrasulfides (DPTT), phosphoryl polysulfides, e.g. Rhenocure® SDT/S from Lanxess Deutschland GmbH and/or
  peroxides, e.g. di-tert.-butyl peroxide, di(tert.-butylperoxy)trimethylcyclohexane, di(tert.-butylperoxyisopropyl)benzene, dicumylperoxides, dimethyldi(tert.-butylperoxy)hexyne, di(tert.-butylperoxy) butylvalerate,
  resorcinol, aldehyde-amine condensates, e.g. hexamethylenetetramine, resorcinol-formaldehyde precondensates and/or vulcanization resins, for example halomethylphenolic resin,
  quinone dioximes
  bisphenols.

Examples of vulcanization accelerators are:
carbamates and triazines, e.g. hexamethylenediamine carbamate (HMDC), organic triazines,
thiazoles, e.g. 2-mercaptobenzothiazole (MBT), zinc mercaptobenzothiazole (ZnMBT), thiadiazoles (TDD),
sulfenamides, for example cyclohexylbenzothiazolesulfenamide (CBS), dibenzothiazyl disulfide (MBTS), butylbenzothiazolesulfenamides (TBBS), dicyclohexyl-benzothiazolesulfenamide (DCBS), 2-(4-morpholinylmercapto)benzothiazole (MBS),
thiurams, for example tetramethylthiuram monosulfide (TMTM), tetraethylthiuram disulfide (TETD), tetramethylthiuram disulfide (TMTD), tetrabenzylthiuram disulfide (TBTD), dipentamethylenethiuram tetra (hexa)sulfide (DPTT),
dithiocarbamates, for example Zn dimethyldithiocarbamates (ZDMC), Cu dimethyldithiocarbamates, Bi dimethyldithiocarbamates, Zn diethyldithiocarbamates (ZDEC), tellurium diethyldithiocarbamates (TDEC), Zn dibutyldithiocarbamates (ZDBC), Zn ethylphenyldithiocarbamates (ZEPC), Zn dibenzyldithiocarbamates (ZBEC), Ni dibutyldithiocarbamates (NBC), selenium diethyldithiocarbamates (SeEDC), selenium dimethyldithiocarbamates (SeDMC), tellurium diethyldithiocarbamates (TeEDC),
thiophosphate and dithiophosphate, e.g. zinc O,O-di-n-butyl dithiophosphate (ZBDP), zinc O-butyl-O-hexyl dithiophosphate, zinc O,O-diisooctyl dithiophosphate (ZOPD), dodecylammonium diisooctyl dithiophosphate (AOPD), e.g. the Rhenogran® grades ZDT, ZAT, ZBOP from Rhein Chemie Rheinau GmbH,
urea/thioureas, e.g. ethylenethiourea (ETU), N,N,N'N'-tetramethylthiourea (TMTU), diethylthiourea (DETU), dibutylthiourea (DBTU), 3-(3,4-dichlorophenyl)-1,1-dimethylurea (diuron) etc., and/or
xanthate accelerators, e.g. zinc isopropyl xanthate (ZIX), guanidines, e.g. diphenylguanidine (DPG) and/or N',N-di-orthotolylguanidine (DOTG) and the guanidine-free replacement accelerators, for example Rhenogran® XLA 60, examples of vulcanization retarders are N-nitrosodiphenylamine, N-cyclohexylthiophthalimide (CPT), e.g. Vulkalent® G), sulfonamide derivates (e.g. Vulkalent® E/C), phthalic anhydride (e.g. Vulkalent® B/C), or benzoic anhydride.

Examples of auxiliaries are dispersion aids, e.g. fatty acids, stearic acid, oleic acid, activators, for example zinc oxide, lead oxide, bismuth oxide, lithium carbonate, sodium carbonate and/or calcium hydroxide, magnesium oxide, and flame retardants, for example antimony oxide, etc.

The abovementioned other fillers, additives, plasticizers, other crosslinking agents, vulcanization accelerators and/or vulcanization retarders, auxiliaries, etc. are familiar to the person skilled in the art and can also be used in granulated form, e.g. in the form of polymer-bound additives or in the form of the crosslinker masterbatches described in EP2314442A.

The rubber mixtures can be further processed, for example to give masterbatches, base mixtures and crosslinkable rubber mixtures.

Masterbatches typically have a high proportion of additives, based on rubber, and comprise by way of example:
  2.5 to 90% by weight of rubber
  0 to 50% by weight of plasticizers
  2 to 80% by weight of silanized pale-colored fillers
  0 to 20% by weight of dispersing agents
  0 to 10% by weight of silane.

Base mixtures are rubber mixtures which, before they are used for practical purposes, require further addition of crosslinking agents and optionally of vulcanization accelerators, for example:
  100 phr of rubber
  0 to 100 phr of plasticizers
  0 to 200 phr of fillers, at least 10% of these being silanized pale-colored fillers
  0 to 30 phr of auxiliaries and
  0 to 10 phr of aging retarders.

Crosslinkable rubber mixtures are rubber mixtures which additionally comprise 0.01 to 20 phr of one or more other crosslinking agents and optionally vulcanization accelerators and optionally vulcanization retarders.

Particular preference is given to crosslinkable rubber mixtures which comprise 30 to 110 phr of carbon black and precipitated silica, 3 to 9 phr of silane, 2 to 7 phr of zinc oxide, and also 0.5 phr to 4 phr of sulfur and 1 to 5 phr of accelerator.

The invention also comprises a method for the production of crosslinkable rubber mixtures comprising at least one silanized pale-colored filler, where one or more further crosslinking agents are added after the production of the rubber mixture comprising at least one silanized pale-colored filler.

The production of the masterbatches, of the base mixture and of the crosslinkable rubber mixture preferably takes place by the methods well known to the person skilled in the art, for example those described in PCT/EP2009/058041. Fillers, auxiliaries, other crosslinking agents and/or aging retarders are mixed here together with the rubber in a mixing assembly. Examples of suitable mixing assemblies are internal mixers, roll units and extruders. Internal mixers with discharge extruder are particularly suitable.

In one embodiment of the invention, the rubber mixture comprising at least one silanized pale-colored filler is produced in a first step by the method of the invention. In a following step, the mixture is homogenized.

In another embodiment of the invention, the rubber mixture comprising at least one silanized pale-colored filler is produced in a first step by the method of the invention. In a following step, the mixture is homogenized. In a following step, one or more further crosslinking agents are added to a further mixing assembly after cooling of the rubber mixture to a temperature below or equal to 130° C. This embodiment is preferably used in the large-scale industrial production of the rubber mixture comprising at least one silanized pale-colored filler, particularly preferably in the production of more than 100 kg.

The phrase "following step" means in this context that the corresponding step must follow the previously mentioned step, but not directly. It is possible that there are also one or more other steps present between the previously mentioned step and the following step.

Particular preference is given here to continuous methods in which the masterbatches or base mixtures, or else the crosslinkable rubber mixtures, are produced in one or more process steps using one or more extruders.

Very particular preference is given to the production method described in DE-A-102008040138 for crosslinkable rubber mixtures, where the base mixture is produced in at least one noncontinuous kneader process, and further crosslinking agents in the form of the crosslinker masterbatches described in EP-A-2314442 are added to the base mixture, and the crosslinker masterbatches are mixed with the base mixture in a continuous process by use of an extruder.

The invention moreover provides a method for the production of vulcanizates comprising the inventive production of crosslinkable rubber mixtures comprising silanized pale-colored fillers and subsequent vulcanization at a temperature in the range of 100° C. to 200° C.

The invention likewise also comprises the use of measurement devices for the determination of the ultrasound wave amplitude a, integrated ultrasound wave amplitude A and/or ultrasound wave intensity i, integrated ultrasound wave intensity I at one or more frequencies in a range of 4 to 10 MHz, preferably of 5 to 7 MHz, for the test method of the invention, for the method of the invention for production of rubber mixtures in general and specifically of crosslinkable rubber mixtures. This also preferably comprises the use of the measurement devices mentioned for the determination of the relative attenuation coefficient $\alpha_{rel}$ in the abovementioned method.

The present invention therefore provides a silanization-checking method which allows in-line monitoring of the in-situ silanization of pale-colored fillers, in particular of precipitated silicas. The method of the invention permits low-cost production of rubber mixtures comprising silanized pale-colored fillers, because production can take place at high temperatures, in particular of above 160° C. The relative attenuation coefficient $\alpha_{rel}$ of the rubber mixture, and also the standard deviation $\sigma$ of the relative attenuation coefficient $\alpha_{rel}$, preferably the moving standard deviation $\sigma_g$, serve for the detection of incipient crosslinking of the rubber mixture.

The method moreover is nondestructive and has high tolerance for carbon black as additional constituent of the rubber mixture.

The headings used in the description are intended merely to serve for subdivision, without any concomitant limiting effect.

The examples, images and figures below serve for illustration of the invention, without any concomitant limiting effect.

EXAMPLES

The components of a typical rubber mixture for tire treads were provided as in table 1:

TABLE 1

Formulation of a typical rubber mixture for tire treads

| Trade name | Ingredients | | Density [g/cm³] | Quantity [phr] |
|---|---|---|---|---|
| Buna ® CB 24 | Butadiene rubber | Lanxess Deutschland GmbH | 0.91 | 15 |
| Buna ® VSL 5025-2 HM | Solution styrene-butadiene rubber | Lanxess Deutschland GmbH | 0.95 | 116.9 |
| Corax ® N-234 | Carbon black | Orion Engineered Carbons GmbH | 1.8 | 35 |
| Ultrasil ® VN3 | Silica | Evonik Industries AG | 2 | 55 |
| ASM-TMQ | Aging retarder 2,2,4-trimethyl-1,2-dihydroquinoline | Lanxess Deutschland GmbH | 1.1 | 3.0 |
| ASM-6PPD | Aging retarder N-1,3-dimethylbutyl-N'-phenyl-p-phenylenediamine | Lanxess Deutschland GmbH | 1 | 2.5 |
| Antilux ® 654 | Aging retarder: mixture of selected paraffins and microwaxes with moderate molecular-weight distribution | Lanxess Deutschland GmbH | 0.9 | 2.0 |
| Aflux ® 37 | Mixture of surface-active substances with fatty acids | Lanxess Deutschland GmbH | 0.98 | 2.0 |
| | Stearic acid | Peter Greven GmbH & Co. KG | 0.89 | 1 |
| Weißsiegel | Zinc oxide | Norzinco GmbH | 5.6 | 2 |
| Si69 | Bis(triethoxysilylpropyl) tetrasulfide | Evonik Industries AG | 0.866 | 4.8 |

These components were mixed in various batches in accordance with the mixing specification in table 2.

TABLE 2

Mixing specification

| Time | Mixture constituent | Note |
|---|---|---|
| 0-0.75' | Polymers | Ram down |
| 0.75'-1'20" | Carbon black, silica + Si69 + ZnO | Ram up |
| 1'20"- 2' | Aging retarder, stearic acid, Aflux ® 37 | Ram off |
| 3.5'-4 | | Turn Ram up |
| 4'-5' | | Ram down |
| 5' | | Discharge |

The mixing parameter rotation rate was varied in accordance with table 3 for the various batches R1M1 to R5M1. R1-R5 here are the various formulations, and M1 is mixing stage 1.

TABLE 3

Process parameters of the internal mixer for the in-situ silanization of a typical rubber mixture from table 1

| Mixing parameter | | Batch | | | | |
|---|---|---|---|---|---|---|
| | | R1M1 | R2M1 | R3M1 | R4M1 | R5M1 |
| Fill level | [%] | 70 | 70 | 70 | 70 | 70 |
| Rotation rate | [rpm] | 40 | 50 | 70 | 100 | 135 |
| Initial temperature | [° C.] | 70 | 70 | 70 | 70 | 70 |
| Mixing time | [min.] | 5 | 5 | 5 | 5 | 5 |
| Discharge temperature $T_A$ | [° C.] | 120 | 135 | 150 | 165 | 180 |

The mixtures R1M1-R5M1 are mixed for 5 min in a 1.5 l (Intermesh) internal mixer from Gumix S.A.

Different values of the mixing temperature are achieved via the differences in rotation rate of the internal mixer. The discharge temperature $T_A$, measured by a method known to the person skilled in the art with use of a needle thermometer directly after discharge of the rubber mixture from the internal mixer, is a measure of the mixing temperature in the internal mixer and therefore of the temperature at which the rubber mixture is produced.

Table 3 shows the discharge temperature $T_A$ of the rubber mixtures with identical composition as a function of the process parameters for the in-situ silanization. The discharge temperature $T_A$ of the mixtures R1M1 and R2M1 are significantly below 160° C. The discharge temperature of R3M1 is 150° C., and this is the reference rubber mixture. The mixtures R4M1 and R5M1 were produced at above 160° C.

The method corresponds to a typical method for in-situ silanization processes in the tire industry for the first mixing stage.

After the mixing process in the internal mixer, the mixture batches were roll-milled on a two-roll mill from Rubicon Gummitechnik und Maschinentechnik GmbH, with temperature-control to 50° C. (cut three times toward the left and three times toward the right), and drawn off to give a milled sheet of the mixture. Strips were cut from the milled sheet. These strips were fed to an EEK32.12L single-screw extruder from Rubicon Gummitechnik und Maschinentechnik GmbH with a low level of mixing action. At the outgoing end of the extruder there is a sensor head equipped with two opposite ultrasound transducers separated by 10 mm, and there is also a temperature sensor T1 with a probe projecting into the flowing mixture, and a pressure/temperature sensor. This temperature sensor measures the pressure p and the temperature T2 at the rubber-metal interface. The width of the flow channel in the sensor head is 20 mm, and its height is 10 mm. The diameter of the ultrasound transducers is 8 mm. Sensor head and extruder were controlled to a temperature of 100° C. The screw rotation rate was 20 rpm. This corresponds to a throughput of about 1 kg of rubber mixture for every 10 min.

The in-line silanization check was implemented by using a pair of K6V1 ultrasound transducers from GE Sensing & Inspection Technologies GmbH in transmission. The ultrasound transducers were controlled by PCM 100LAN test electronics from Inoson GmbH. The piezoelectric effect was used to generate the ultrasound pulses every 150 ms in the ultrasound transducer. The ultrasound transducer converts the voltage pulses to ultrasound signals. The ultrasound transducers were excited here with 7 bursts at the intrinsic frequency of the ultrasound transducer: 6 MHz. The ultrasound pulse from the transmitter passes through the rubber mixture that is being extruded, and is attenuated here by the rubber mixture. The oscillation amplitude a of the ultrasound signal is reduced. The receiver receives the acoustic signal and converts it to a voltage signal. The voltage signal is amplified (35 to 40 dB) by the hardware of the PCM100LAN, and passed to a computer. The computer uses what is known as Fast Fourier Transformation (FFT) to evaluate the first acoustic pulse of the "A scan". The amplitude spectrum a(f) thus obtained as a function of the ultrasound frequency f was integrated between 5.8 and 6.2 MHz (cf. table 4), and the logarithm was calculated. The values thus obtained, ln $A(f_{min.},f_{max.})$ for the logarithmic integral were plotted for the various mixture batches R1M1 to R5M1 as a function of the time t for 7.5 min together with the values from the temperature sensors T1 and T2, and also the pressure values. The time $t_{oF}$ required by the acoustic signal for transmission from the piezo crystal of the emitter to the piezo crystal of the receiver was additionally determined. This is achieved before discharge of the mixture from the sensor head at the outgoing end of the extruder. The residence time of the mixture in the sensor head was less than 1 minute.

The relative attenuation coefficient $\alpha_{rel}(f_{min.},f_{max.})$ is calculated from the values for ln $A(f_{min.},f_{max.})$ by the Lambert Beer law.

$$\alpha_{rel}(f_{min.},f_{max.})=(\ln A_{ref.}(f_{min.},f_{max.})-\ln A(f_{min.},f_{max.}))/x \quad (1d)$$

x here is the distance between the ultrasound transducers. In formula (1d), the average value of ln $A_{ref.}(f_{min.},f_{max.})$ is 4.06 a.u. for the reference extrudate R3M1 (with a mixing temperature between 140° C. and 160° C.) for an extrusion time of Δt=7.5 min. The distance between the acoustic transducers was 10 mm.

Figure 1:
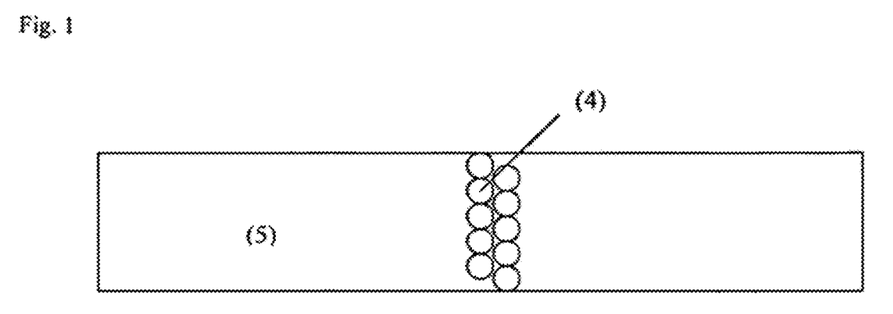
FIG. 1 describes in plan view by way of example the detection band, consisting of the ultrasound sensor pairs (4), i.e. one sender and one receiver for each pair, and of the flow channel (5).
Figure 2:
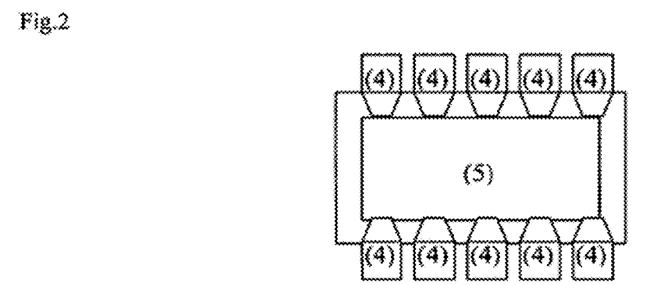
FIG. 2 depicts a side view of the arrangement in FIG. 1.
Figure 3:
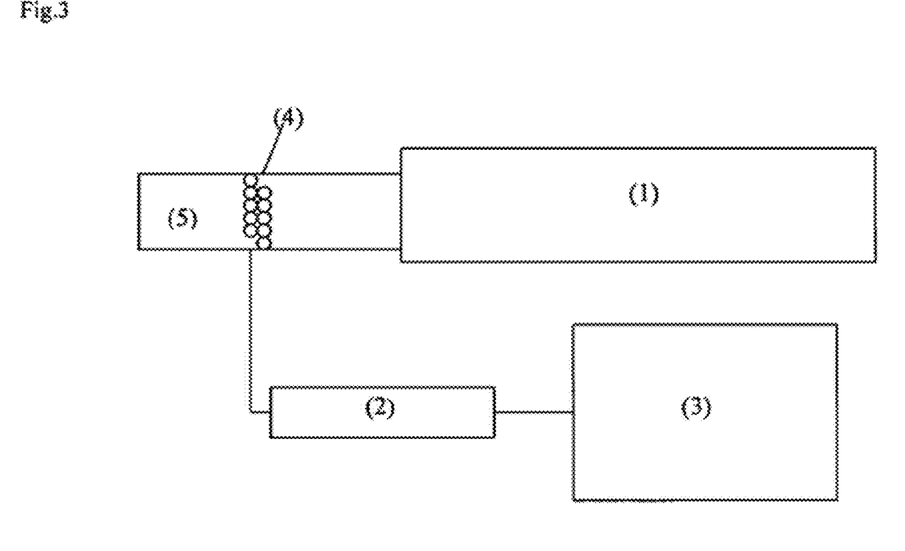
FIG. 3 shows an arrangement of an extruder (1), the detection band, consisting of the ultrasound transducer pairs (4) and the flow channel (5), and the ultrasound-check electronics (2), and a computer as evaluation unit (3).
Figure 4:
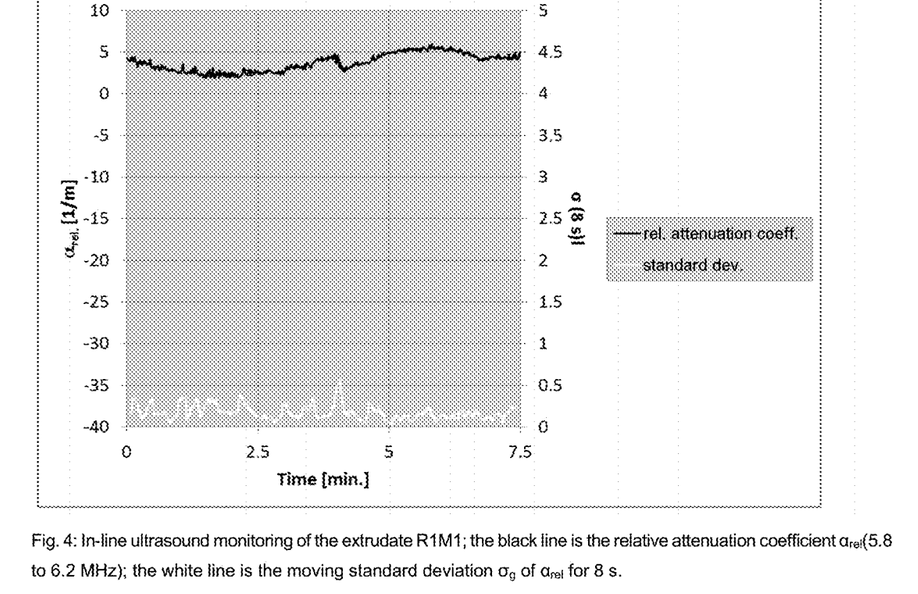
Figure 5:
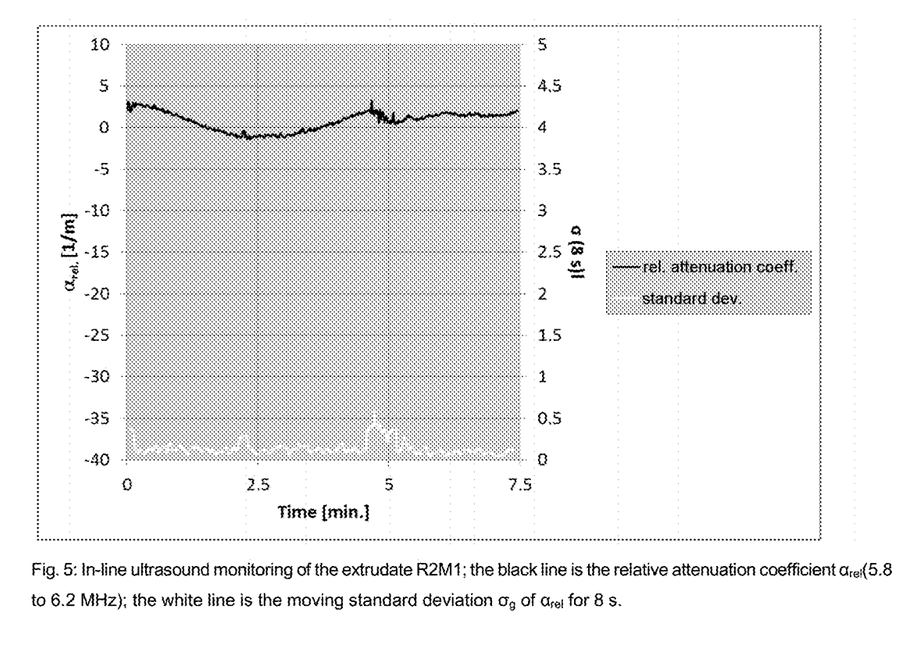
Figure 6:
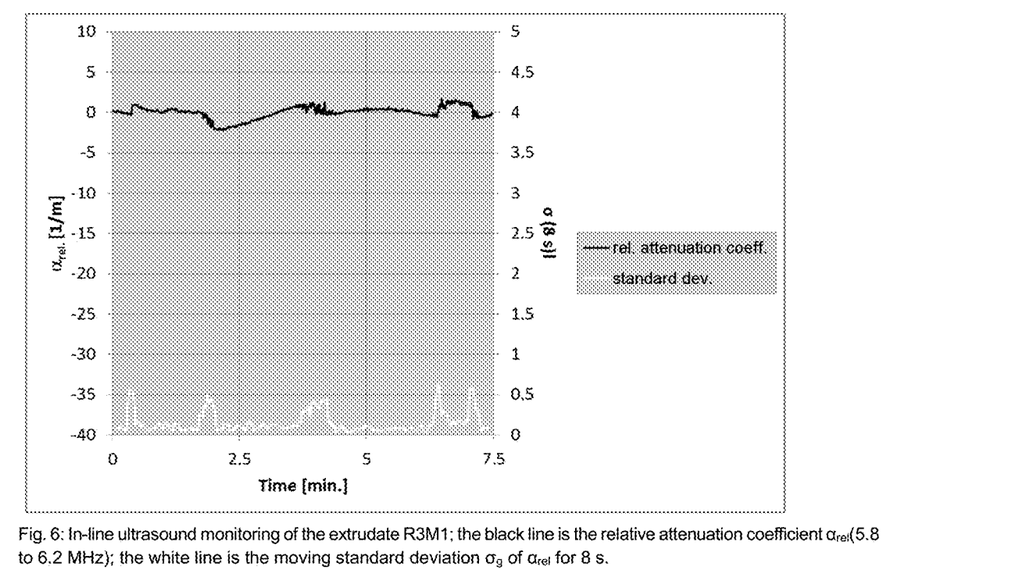
Figure 7:
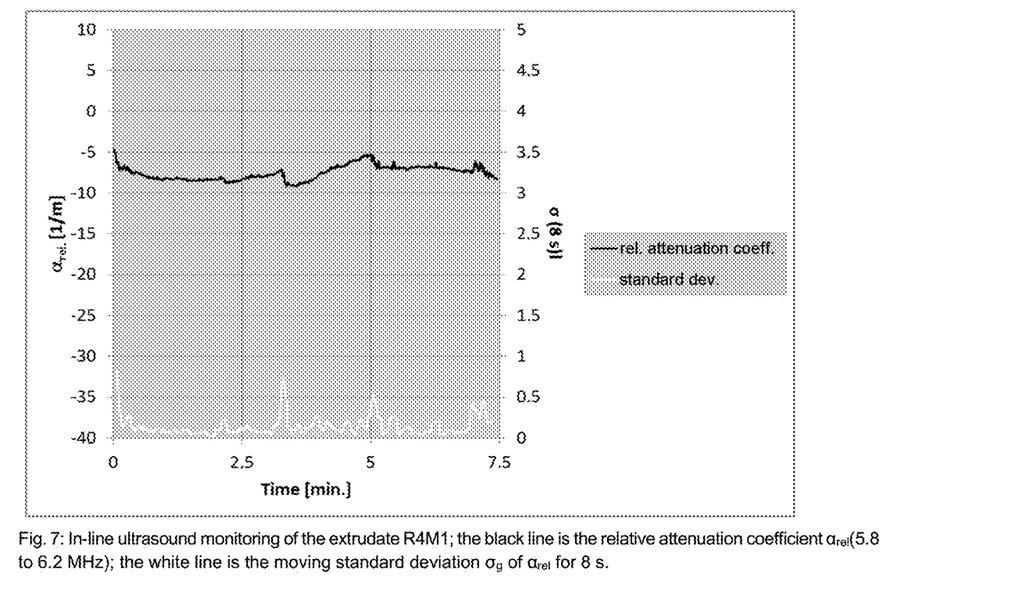
Figure 8:
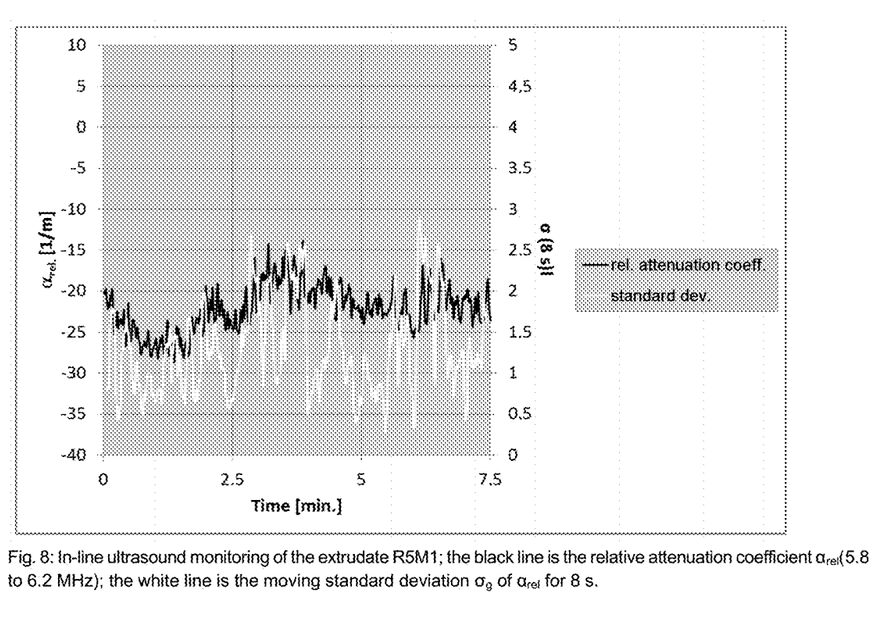

The result for the frequency range $f_{min.}$=5.8 MHz to $f_{max.}$=6.2 MHz for each extrudate is depicted in images 1 to 5.

Table 4 presents the average values for the relative attenuation coefficient $\alpha_{rel}(f_{min.},f_{max.})$ for a period of $\Delta t$=7.5 min for the extrusion of each mixture batch, corresponding to images 1 to 5. These average values were calculated in accordance with formula (1e). In each case, the average value of the standard deviation a of the relative attenuation coefficient $\alpha_{rel}(f_{min.},f_{max.})$ for $\Delta t$=7.5 min was moreover determined in accordance with formula (1f).

Table 4 also states the moving standard deviation $\sigma_g$ over a period of 8 s. The moving standard deviation $\sigma_g$ is calculated in accordance with formula (1h) from the moving average of $\alpha_{rel}$, calculated in accordance with formula (1g).

Images 1 to 5 depict the moving value of the standard deviation $\sigma_g$ for each measurement point n at the juncture t(n) for a time interval comprising 51 measurement points (x=y=25) from t(n−25) to t(n+25). The letter n here indicates the number of the measurement point. The standard deviation $\sigma_g$ is determined by using 25 measured values before the juncture t(n), the measured value at the juncture t(n) and the 25 measured values after the juncture t(n). The phrase "moving value" means that the standard deviation $\sigma_g$ is determined for the following measurement point n+1 at the juncture t(n+1) in the time interval t(n−24) to t(n+26). The time interval composed of 51 measurement points for the determination of $\sigma_g$ is therefore shifted by one measurement point. The moving standard deviation $\sigma_g$ of $\alpha_{rel}(f_{min.},f_{max.})$ in images 1 to 5 was determined within a time interval of 8 s.

The average value for the pressure sensor p and the average values for the temperature sensor T1 with probe and T2 without probe are additionally stated. The velocity of sound $V_S$ is determined from the distance x and the time $t_{oF}$ to the first voltage amplitude. It is necessary here to take into account the lead time $t_{US}$=4.6 μs of the ultrasound signal in both ultrasound transducers in accordance with formula (2).

$$V_S = x/(t_{oF} - t_{US}) \quad (2)$$

In addition to the characteristic ultrasound values, the Mooney ML1+4 (100° C.) viscosity was determined.

TABLE 4

Results of the measurements on the rubber mixtures during extrusion (measurement conditions and characteristic ultrasound values), and also on the extruded rubber mixtures (Mooney viscosity and RPA 2000) from table 3. The standard deviation from the average value is stated with "±" after the average value.

| Batch | Unit | R1M1 | R2M1 | R3M1 | R4M1 | R5M1 |
|---|---|---|---|---|---|---|
| Standard process monitoring | | | | | | |
| Mooney ML1 + 4 (100° C.) viscosity | [MU] | 106 | 101 | 99 | 97 | 112 |
| RPA 2000 G'(1%, 1 Hz, 60° C.) | [kPa] | 1145 | 1070 | 1032 | 941 | 876 |
| Measurement conditions | | | | | | |
| Pressure p | [bar] | 72 ± 1 | 69 ± 1 | 68 ± 1 | 68 ± 1 | 74 ± 2 |
| T1 | [° C.] | 95 ± 1 | 95 ± 1 | 95 ± 1 | 95 ± 1 | 95 ± 1 |
| T2 | [° C.] | 104 ± 1 | 103 ± 1 | 103 ± 1 | 103 ± 1 | 103 ± 1 |
| Characteristic ultrasound values | | | | | | |
| $V_S$ | [m/s] | 1331 ± 1 | 1329 ± 1 | 1328 ± 1 | 1326 ± 2 | 1331 ± 2 |
| Relative attenuation coefficient $\alpha_{rel}$ (5.8 MHz to 6.2 MHz) | [1/m] | 4 ± 1 | 1 ± 1 | 0 ± 1 | −8 ± 1 | −22 ± 3 |
| Moving standard deviation $\sigma_g$ of $\alpha_{rel}$ for 8 s | [1/m] | 0.2 | 0.1 | 0.2 | 0.1 | 1.3 |

Table 4 shows that for rubber mixtures the value of the dynamic storage modulus G' (1%, 1 Hz, 60° C.) decreases with increasing discharge temperature $T_A$ (cf. table 3).

The Mooney ML1+4 (100° C.) viscosity values initially likewise decrease with increasing discharge temperature $T_A$ in accordance with progressive silanization of the silica surface. However, R5M1 exhibits a large increase of Mooney ML1+4 (100° C.) viscosity in comparison with R4M1 and R3M1. R4M1 and R3M1 have not yet undergone incipient crosslinking, whereas R5M1 has.

It is apparent in table 4, and also in images 1 to 5, that the acoustic attenuation coefficient $\alpha_{rel}$ correspondingly decreases with increasing discharge temperature of the rubber mixtures. The values of the relative acoustic attenuation coefficient $\alpha_{rel}$ correlate here with the storage modulus G'(1%, 1 Hz, 60° C.). The attenuation coefficient $\alpha_{rel}$ resembles the storage modulus G'(1%, 1 Hz, 60° C.) in being a measure of the efficiency of silanization of the silica surface if the rubber mixtures R1M1 to R5M1 are established at comparable values for pressure and temperature during ultrasound measurement. As table 3 shows, this is the case.

The relative attenuation coefficient $\alpha_{rel}$ of the extrudate R5M1 is significantly below 0 [1/m], with a value of −22 [1/m].

Another very significant difference of the extrudate R5M1, in comparison with R1M1 to R4M1, is the moving standard deviation $\sigma_g$ of the values for $\alpha_{rel}$ in small time intervals of <15 s. The line relating to the values for ard of the extrudate R5M1 (image 5) fluctuates to a significantly greater extent than the lines relating to R1M1 to R4M1 (images 1 to 4). Accordingly, the average value of the moving standard deviation $\sigma_g$ of $\alpha_{rel}$ for 8 s in table 4 for the extrudates R1M1 to R4M1 is small: 0.1 m$^{-1}$ and, respectively, 0.2 m$^{-1}$. The moving standard deviation $\sigma_g$ of $\alpha_{rel}$ for 8 s for R5M1 with a discharge temperature $T_A$ of 180° C. is very large: 1.3 m$^{-1}$. R5M1 has undergone incipient crosslinking; this correlates with the high Mooney ML1+4 (100° C.) viscosity of R5M1.

The standard deviation $\sigma_g$ of the relative attenuation coefficient $\alpha_{rel}$ over the entire extrusion time of 7.5 min is 1 m$^{-1}$ for the extrudates R1M1 to R4M1 and 3 m$^{-1}$ for R5M1. However, with the long time interval of 7.5 min, the relative difference of the standard deviations σ between the extrudates R1M1 to R4M1 and R5M1 is significantly smaller than that of the moving standard deviations $\sigma_g$. The reason for this is that over a prolonged time interval even small fluctuations in the measurement conditions and/or extrusion parameters make a contribution to the standard deviation, and the total standard deviation value therefore increases.

Detection of incipient crosslinking of a rubber mixture can accordingly preferably be defined by way of the moving standard deviation $\sigma_g$ of $\alpha_{rel}$ over a period of 1 to 100 s, particularly preferably of 1 to 50 s, very particularly preferably of 1 to 15 s, in the present case 8 s.

The comparable values for the velocity of sound $V_S$ in all batches R1M1 to R5M1 proves that mixing temperature, pressure and composition of the mixture batches are uniform.

What is claimed is:

1. A method for checking the silanization of pale-colored fillers, comprising:
    irradiating a rubber mixture comprising at least one silanized pale-colored filler and at least one rubber with ultrasound waves in a frequency range of 4 to 10 MHz, wherein the rubber mixture is produced at a temperature of above 160° C., and
    determining the signal strength of the ultrasound waves after transmission through the rubber mixture, where a relative attenuation coefficient $\alpha_{rel}$ of the rubber mixture in the frequency range of the ultrasound waves is determined, a standard deviation σ of the relative attenuation coefficient $\alpha_{rel}$ is determined, and $\alpha_{rel}$ and σ are used for detection of incipient crosslinking of the rubber mixture,
    wherein the incipient crosslinking of the rubber mixture is detected in that the standard deviation σ of the relative attenuation coefficient $\alpha_{rel}$ of the incipiently crosslinked rubber mixture is above 0.5 (1/m) and the relative attenuation coefficient $\alpha_{rel}$ of the incipiently crosslinked rubber mixture is below 0 (1/m).

2. The method as claimed in claim 1, wherein the moving standard deviation $\sigma_g$ of the relative attenuation coefficient $\alpha_{rel}$ of the incipiently crosslinked rubber mixture, produced at a temperature of above 160° C., is above 1 (1/m), based on a measurement time of 1 to 50 s and the relative attenuation coefficient $\alpha_{rel}$ of the incipiently crosslinked rubber mixture, produced at a temperature of above 160° C., is below 0 (1/m).

3. The method as claimed in claim 1, wherein the at least one silanized pale-colored filler is produced from at least one pale-colored filler and at least one silanizing agent.

4. The method as claimed in claim 3, wherein the rubber mixture comprises less than 10 phr of crosslinking agent other than the at least one silanizing agent and the at least one silanized pale-colored filler.

5. The method as claimed in claim 1, wherein the standard deviation σ is the moving standard deviation $\sigma_g$.

6. The method as claimed in claim 1, wherein the mixture is extruded and the resultant extrudate is irradiated with sound.

7. The method for the production of a rubber mixture comprising at least one silanized pale-colored filler where, at a temperature of above 160° C., at least one pale-colored filler is mixed with at least one rubber and with at least one silanizing agent, and where at least a portion of the resultant rubber mixture is checked by the method as claimed in claim 1.

8. The method as claimed in claim 7, wherein the method for the production of a rubber mixture comprising at least one silanized pale-colored filler is implemented at a temperature of above 160° C. to 200° C.

9. The method as claimed in claim 7, where the moving standard deviation $\sigma_g$ of the relative attenuation coefficient $\alpha_{rel}$ of the rubber mixture is below 0.5 (1/m) based on a measurement time of 1 to 100 s and the relative attenuation coefficient $\alpha_{rel}$ of the rubber mixture is below 0 (1/m) and equal to or above −15 (1/m).

10. The method as claimed in claim 1, wherein the at least one pale-colored filler is selected from the group consisting of mica, kaolin, siliceous earth, calcium carbonates, zinc oxide, aluminum oxide, titanium dioxide, silicas, chalk and talc.

11. The method as claimed in claim 3, wherein the at least one silanizing agent is a silane selected from the group consisting of bis(3-triethoxysilypropyl) tetrasulfide, bis(triethoxysilylpropyl) disulfide, 3-thiocyanatopropyltriethoxysilane, 3-mercaptopropyldi (tridecan-1-oxy-13-penta (ethyleneoxide)) ethoxysilane, gamma-mercaptopropyltrimethoxysilane, and bis (3-triethoxysilypropyl) tetrasulfide.

12. A method for the production of crosslinkable rubber mixtures comprising at least one silanized pale-colored filler, where one or more further crosslinking agents are added after the production of the rubber mixture as claimed in claim 7.

13. A method for the production of vulcanizates comprising the production of crosslinkable rubber mixtures comprising silanized pale-colored fillers as claimed in claim 12 and subsequent vulcanization at a temperature in the range of 100° C. to 200° C.

* * * * *